United States Patent
Kim et al.

(10) Patent No.: US 11,819,510 B2
(45) Date of Patent: Nov. 21, 2023

(54) FOOD COMPOSITION FOR AMELIORATING CEREBROVASCULAR DISEASES CONTAINING 2'-FUCOSYLLACTOSE AND PHARMACEUTICAL COMPOSITION FOR PREVENTING OR TREATING CEREBROVASCULAR DISEASES CONTAINING 2'-FUCOSYLLACTOSE

(71) Applicant: Advanced Protein Technologies Corp., Suwon-si (KR)

(72) Inventors: Kyung Ho Kim, Daegu (KR); Chul Soo Shin, Suwon-si (KR); Jong Won Yoon, Seongnam-si (KR); Seon Min Jeon, Daegu (KR); Young Ha Song, Yongin-si (KR); Ok Seon Jeon, Hwaseong-si (KR)

(73) Assignee: Advanced Protein Technologies Corp., Suwon-si (KR)

( * ) Notice: Subject to any disclaimer, the term of this patent is extended or adjusted under 35 U.S.C. 154(b) by 0 days.

(21) Appl. No.: 17/993,770

(22) Filed: Nov. 23, 2022

(65) Prior Publication Data

US 2023/0122074 A1    Apr. 20, 2023

Related U.S. Application Data

(63) Continuation of application No. PCT/KR2021/006498, filed on May 25, 2021.

(30) Foreign Application Priority Data

Sep. 14, 2020 (KR) .......................... 10-2020-0117861
Sep. 14, 2020 (KR) .......................... 10-2020-0117862
May 13, 2021 (KR) .......................... 10-2021-0061963

(51) Int. Cl.
*A61K 31/702* (2006.01)
*A61P 7/02* (2006.01)

(52) U.S. Cl.
CPC .............. *A61K 31/702* (2013.01); *A61P 7/02* (2018.01)

(58) Field of Classification Search
None
See application file for complete search history.

(56) References Cited

U.S. PATENT DOCUMENTS

| | | | |
|---|---|---|---|
| 6,589,992 B2 * | 7/2003 | Uckun | A61K 31/277 514/626 |
| 2006/0166284 A1 * | 7/2006 | Light | G01N 33/86 435/7.5 |
| 2015/0320778 A1 | 11/2015 | Chow et al. | |
| 2015/0342974 A1 * | 12/2015 | Chow | A23P 10/40 514/61 |
| 2016/0287619 A1 * | 10/2016 | Vigsnæs | A61K 35/745 |

FOREIGN PATENT DOCUMENTS

| | | |
|---|---|---|
| JP | 2002-363100 E | 12/2002 |
| KR | 10-2010-0138438 A | 12/2010 |
| KR | 10-1682108 B1 | 12/2016 |
| KR | 10-1717240 B1 | 3/2017 |
| KR | 10-1740519 B1 | 6/2017 |
| KR | 10-1897629 B1 | 9/2018 |
| KR | 10-2019-0130720 A | 11/2019 |
| KR | 10-2127706 B1 | 6/2020 |
| KR | 10-2241938 B1 | 4/2021 |
| WO | 2016/046294 A1 | 3/2016 |

OTHER PUBLICATIONS

Shin et al. KR 10-2019-0130720 A, Nov. 2019, machine-translated from Dialog on Mar. 7, 2023 (Year: 2019).*
David S. Newburg et al., "Lactodifucoterraose, a human milk oligosaccharide, attenuates platelet function and inflammatory cytokine release", J Thromb Thrombolysis, 2016, pp. 46-55, vol. 42.
Korean Office Action for 10-2020-0117862 dated Nov. 17, 2020.
Korean Office Action 10-2021-0061963 dated Jul. 15, 2021.
International Search Report for PCT/KR2021/006498 dated Aug. 27, 2021 (PCT/ISA/210).

* cited by examiner

*Primary Examiner* — Dale R Miller
(74) *Attorney, Agent, or Firm* — Sughrue Mion, PLLC

(57) ABSTRACT

Disclosed are a food composition containing 2'-fucosyllactose and a pharmaceutical composition containing 2'-fucosyllactose that are effective in ameliorating, preventing or treating various cerebro-cardiovascular diseases caused by thrombogenesis, and a method for ameliorating a cerebro-cardiovascular disease caused by a thrombus by administering a composition including 2'-fucosyllactose (2'-FL) to a subject in need thereof. The 2'-fucosyllactose (2'-FL) exhibits antagonistic (inhibitory) activity against CRP and collagen, which are agonists of platelets, and thus can be used to inhibit thrombogenesis due to abnormal platelet activity.

4 Claims, 10 Drawing Sheets

FOOD COMPOSITION FOR AMELIORATING CEREBROVASCULAR DISEASES CONTAINING 2'-FUCOSYLLACTOSE AND PHARMACEUTICAL COMPOSITION FOR PREVENTING OR TREATING CEREBROVASCULAR DISEASES CONTAINING 2'-FUCOSYLLACTOSE

CROSS-REFERENCE TO RELATED APPLICATIONS

This application is a Bypass Continuation of PCT/KR2021/006498 filed on May 25, 2021, which is based on and claims priority from Korean Patent Application No. 10-2020-0117862 filed on Sep. 14, 2020, Korean Patent Application No. 10-2020-0117861 filed on Sep. 14, 2020, and Korean Patent Application No. 10-2021-0061963 filed on May 13, 2021, the entire disclosures of which are incorporated herein by reference.

BACKGROUND OF THE INVENTION

Field of the Invention

The present invention relates to a composition for ameliorating, preventing or treating cerebro-cardiovascular diseases caused by thrombogenesis containing 2'-fucosyllactose, and a method for ameliorating a cerebro-cardiovascular disease caused by a thrombus by administering a composition including 2'-fucosyllactose (2'-FL) to a subject in need thereof. More particularly, the present invention relates to a food composition containing 2'-fucosyllactose and a pharmaceutical composition containing 2'-fucosyllactose that are effective in ameliorating various cerebro-cardiovascular diseases caused by thrombogenesis, such as blood circulation disorders, arteriosclerosis, thrombosis, hypertension, myocardial infarction, angina pectoris, and stroke.

Description of the Related Art

The westernization of diet and lifestyle and the increase in the elderly population have brought about a great increase in the incidence of cerebro-cardiovascular diseases, which are caused by blood circulation disorders. Statistics on causes of death in 2018 show that among the top 10 leading causes of death, heart diseases, cerebrovascular diseases, and hypertension-related diseases ranked second, fourth, and tenth, respectively. Cerebro-cardiovascular diseases are emerging as a serious social problem.

Factors involved in blood circulation may be broadly divided into those related to blood cells and to blood coagulation. Platelet adhesion to prevent bleeding due to blood vessel damage, hemostasis attributable to plug formation, and thrombogenesis and vascular occlusion due to abnormally excessive platelet formation in pathophysiological conditions are pathologic factors causing vascular diseases.

Therefore, it is necessary to continuously consume food or to administer drugs capable of removing blood clots and of inhibiting thrombogenesis. However, conventional drugs for improving blood circulation are difficult to administer due to side effects such as gastrointestinal disorders and increased blood pressure. Therefore, there is a need to develop a product that has few side effects and is thus safe for the human body while fundamentally ameliorating blood circulation disorders by suppressing thrombogenesis.

Meanwhile, 200 or more types of human milk oligosaccharides (HMO) having specific structures are present at a much higher concentration (5-15 g/L) in human milk than in milk of other mammals. It is reported that HMO is involved in a variety of biological activities, such as a prebiotic effect of promoting the growth of intestinal lactic-acid bacteria, an effect of preventing pathogen infection, an effect of regulating the immune system, and beneficial influences on infant growth, brain development and health.

HMOs contain D-glucose (Glc), D-galactose (Gal), N-acetylglucosamine (GlcNAc), L-fucose (Fuc), and sialic acid [Sia; N-acetyl neuraminic acid (Neu5Ac)]. HMOs have a very diverse and complicated structure, so about 200 isomers having different residues and glycosyl bonds may be present at different polymerization degrees (DP 3-20). However, despite the complicated structure, HMOs have several structures in common. Most HMOs have a lactose (Galβ1-4Glc) residue at the reducing end thereof. The Gal of lactose is sialylated in the form of 3-sialyllactose or 6-sialyllactose with an α-aminooxy(2,3)- or α-(2,6)-bond, respectively, or is fucosylated in the form of 2'-fucosyllactose (2-FL) or 3-fucosyllactose (3-FL) with an α-(1,2)- or α-(1,3) bond, respectively.

About 200 different complex oligosaccharides are found in human milk. 137 fucosylated oligosaccharides, including three types of oligosaccharides having the highest content, are present in an amount of about 77%, whereas most of the remaining oligosaccharides are 30 sialylated oligosaccharides, which are present in an amount of about 28%. Among them, in particular, 2'-fucosyllactose and 3-fucosyllactose are reported to be major HMOs involved in the aforementioned various biological activities.

The present invention is based on the development of a material that can be used for the amelioration, prevention, or treatment of cerebro-cardiovascular diseases caused by thrombosis using HMOs, which are derived from human milk and are verified to be safe.

SUMMARY OF THE INVENTION

Therefore, the present invention has been made in view of the above problems, and it is an object of the present invention to provide an HMO-based food composition that is effective in ameliorating various cerebro-cardiovascular diseases caused by thrombogenesis, such as blood circulation disorders, arteriosclerosis, thrombosis, hypertension, myocardial infarction, angina pectoris, and stroke, and an HMO-based pharmaceutical composition that is effective in preventing or treating such cerebro-cardiovascular diseases.

In accordance with the present invention, the above and other objects can be accomplished by the provision of a food composition for ameliorating a cerebro-cardiovascular disease caused by a thrombus containing 2'-fucosyllactose (2'-FL).

The thrombus may be formed due to blood clotting by platelets.

The blood clotting by platelets may be caused by an action of collagen-related peptide (CRP) or collagen, which is an agonist of platelets.

The cerebro-cardiovascular disease may be any one selected from blood circulation disorders, arteriosclerosis, thrombosis, hypertension, myocardial infarction, angina pectoris, and stroke.

In accordance with another aspect of the present invention, provided is a pharmaceutical composition for preventing or treating a cerebro-cardiovascular disease caused by a thrombus containing 2'-fucosyllactose (2'-FL).

The thrombus may be formed due to blood clotting by platelets.

The blood clotting by platelets may be caused by an action of collagen-related peptide (CRP) or collagen, which is an agonist of platelets.

The cerebro-cardiovascular disease may be any one selected from blood circulation disorders, arteriosclerosis, thrombosis, hypertension, myocardial infarction, angina pectoris, and stroke.

In another embodiment, the present disclosure provides a method for ameliorating a cerebro-cardiovascular disease caused by a thrombus, comprising administering a composition comprising 2'-fucosyllactose (2'-FL) to a subject in need thereof. In some embodiment, the thrombus is formed due to blood clotting by platelets. In another embodiment, the blood clotting by platelets is caused by an action of collagen-related peptide (CRP) or collagen, which is an agonist of platelets. In one embodiment, the cerebro-cardiovascular disease is any one selected from blood circulation disorders, arteriosclerosis, thrombosis, hypertension, myocardial infarction, angina pectoris, and stroke.

BRIEF DESCRIPTION OF THE DRAWINGS

The above and other objects, features, and other advantages of the present invention will be more clearly understood from the following detailed description taken in conjunction with the accompanying drawings, in which.

DETAILED DESCRIPTION OF THE INVENTION

Figure 1:
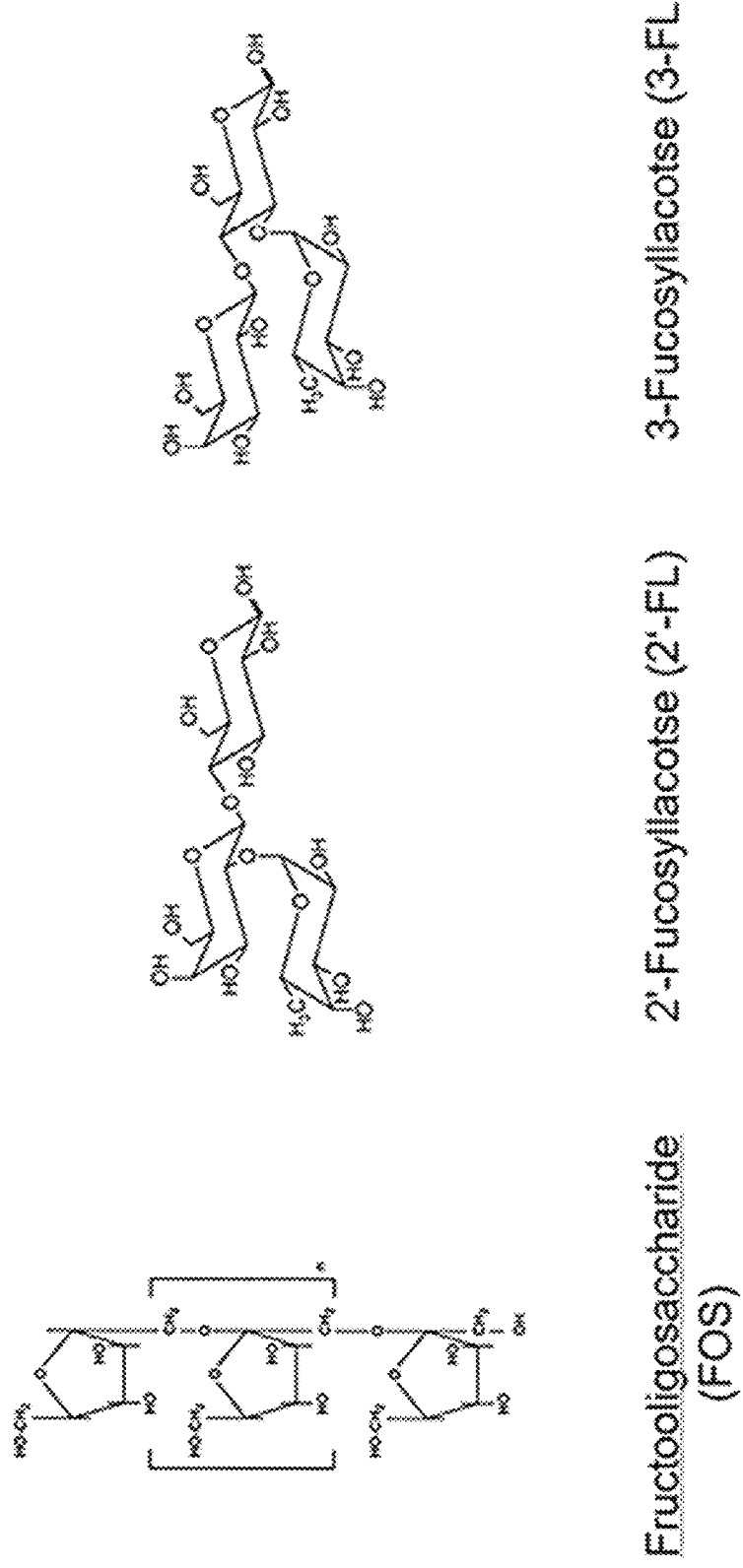
FIG. 1 illustrates the structures of fructooligosaccharide (FOS), 2'-fucosyllactose, and 3-fucosyllactose used in the experiments of the present invention.
Figure 2A:
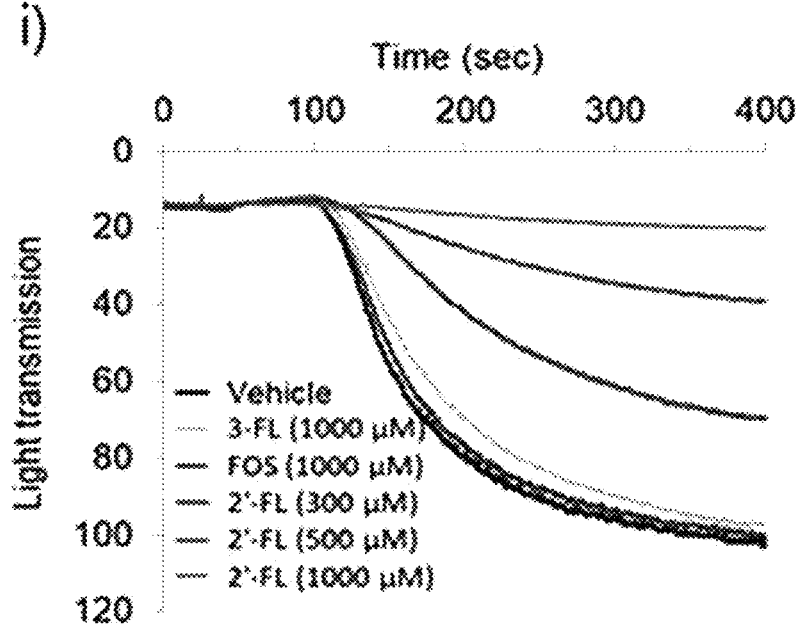
FIGS. 2A-2D illustrate the inhibitory effect of HMOs on platelet aggregation.
Figure 2A:
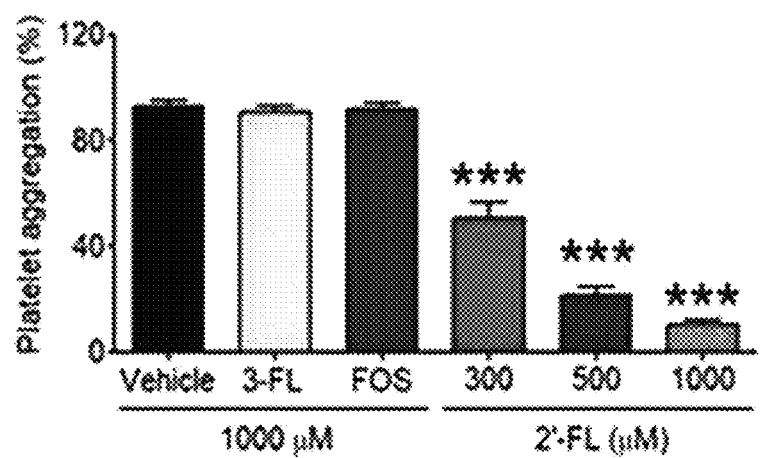
Figure 2B:
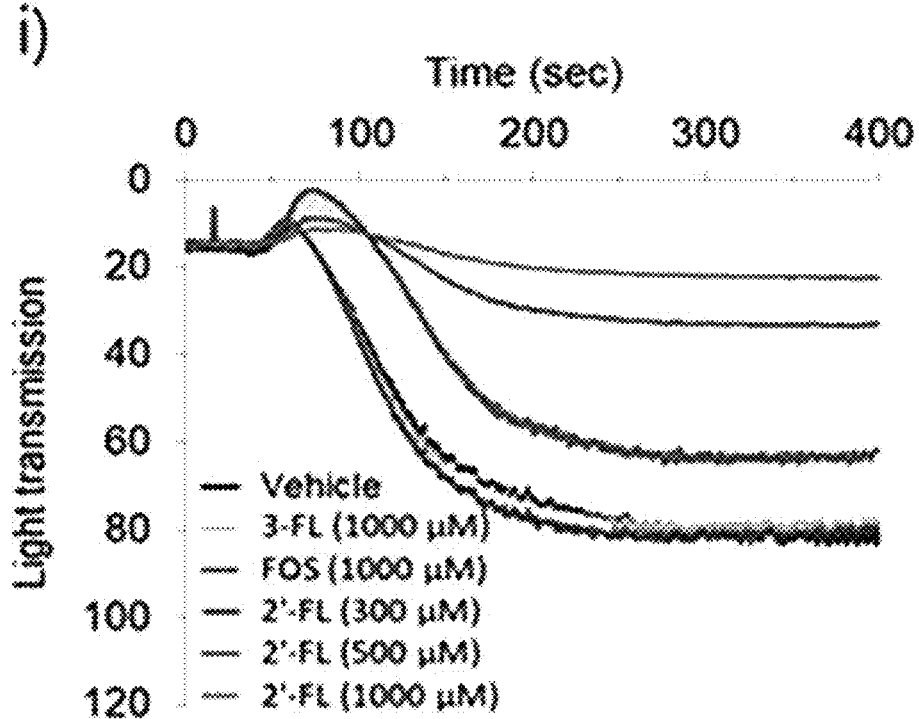
Figure 2B:
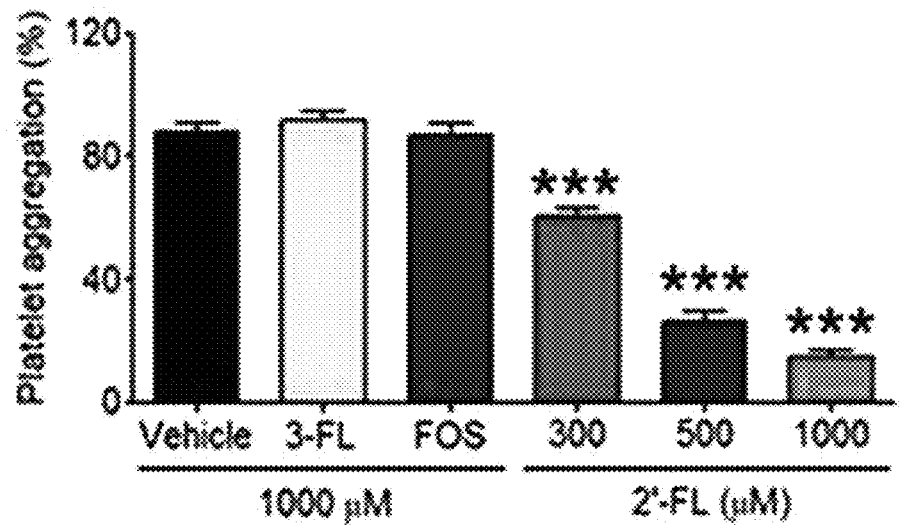
Figure 2C:
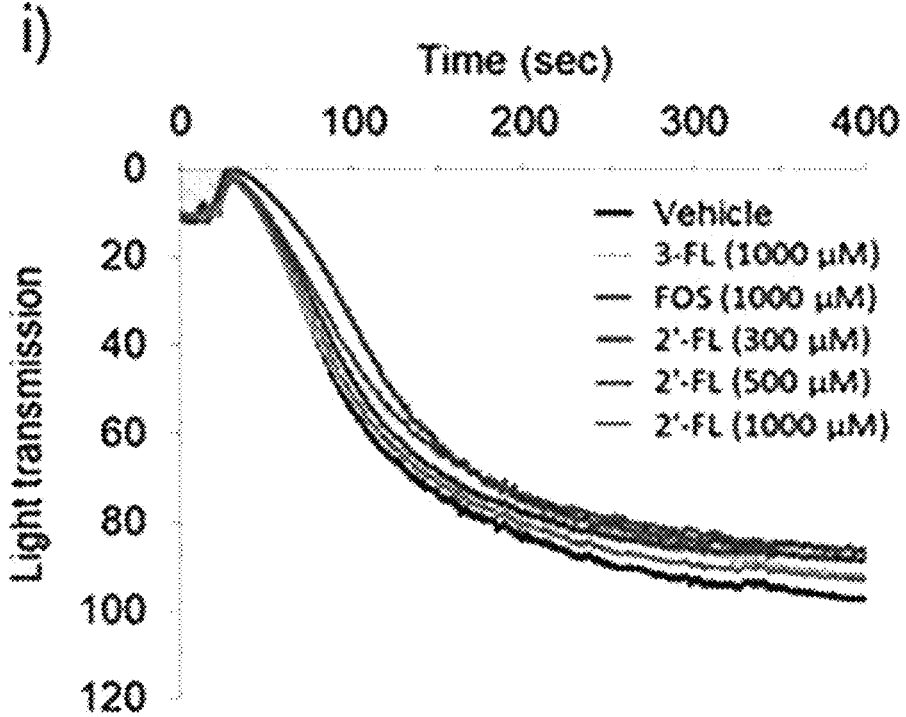
Figure 2C:
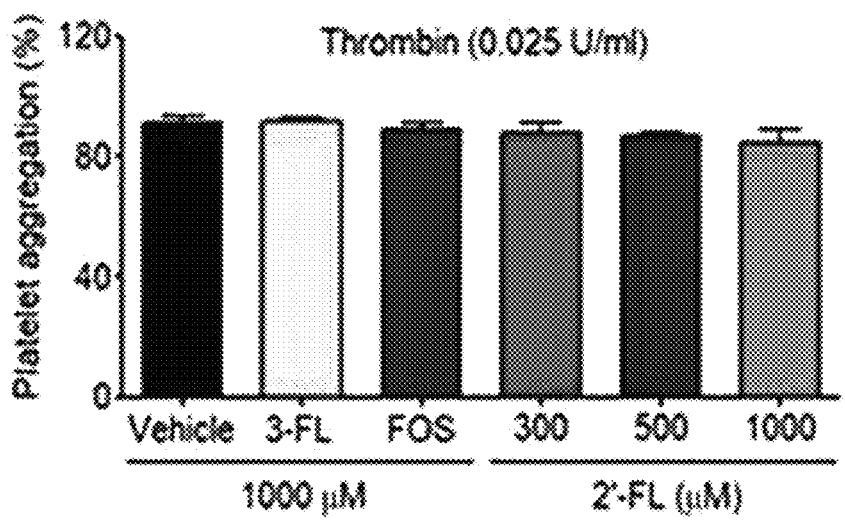
Figure 2D:
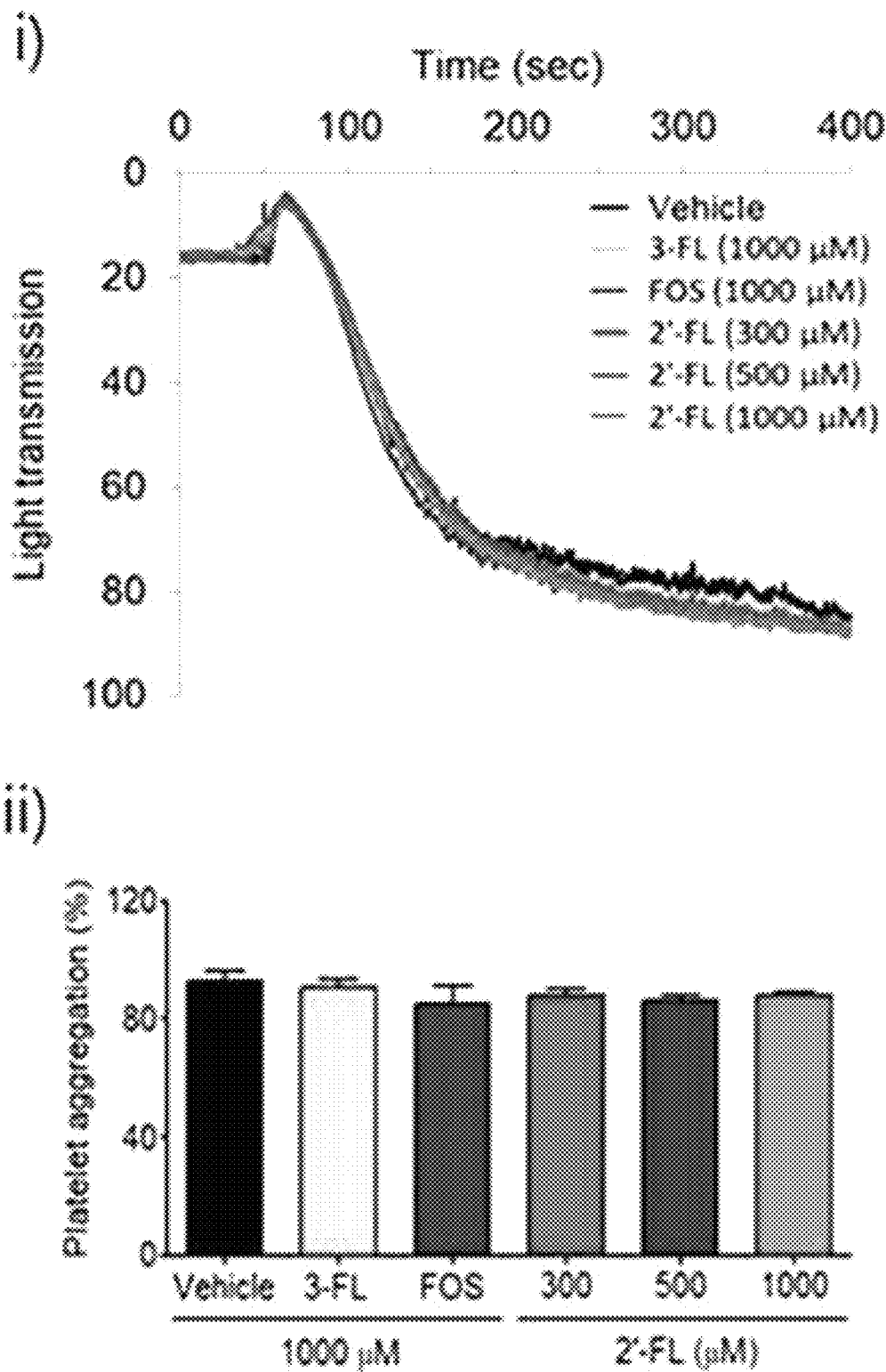

The present invention provides a food composition for ameliorating cerebro-cardiovascular diseases caused by thrombus containing 2'-fucosyllactose. The present invention also provides a pharmaceutical composition for preventing or treating cerebro-cardiovascular diseases caused by thrombus containing 2'-fucosyllactose. In this case, the cerebro-cardiovascular disease may be selected from blood circulation disorders, arteriosclerosis, thrombosis, hypertension, myocardial infarction, angina pectoris, and stroke.

In the food composition for ameliorating cerebro-cardiovascular diseases and the pharmaceutical composition for preventing or treating cerebro-cardiovascular diseases according to the present invention, the thrombus may preferably be caused by blood clotting by platelets. Here, the blood clotting by platelets may preferably be caused by the action of CRP or collagen, which is an agonist of platelets.

In the food composition for ameliorating cerebro-cardiovascular diseases and the pharmaceutical composition for preventing or treating cerebro-cardiovascular diseases according to the present invention, 2'-fucosyllactose of the present invention preferably inhibits the agonist action of CRP or collagen, which is an agonist of platelets, on platelets. That is, it can be inferred that the 2'-fucosyllactose of the present invention acts on platelet aggregation signaling pathway mediated by GPVI (glycoprotein VI; a glycoprotein receptor for collagen) to inhibit platelet activation.

In the food composition for ameliorating cerebro-cardiovascular diseases and the pharmaceutical composition for preventing or treating cerebro-cardiovascular diseases according to the present invention, 2'-fucosyllactose of the present invention preferably inhibits the agonist action of thrombin, which is an agonist of platelets, on platelets. That is, it can be inferred that the 2'-fucosyllactose of the present invention does not exhibit an inhibitory effect on platelet activation mediated by a GPCR (G-protein coupled receptor) signaling pathway.

Blood from healthy people does not coagulate in blood vessels, but due to the cause such as damage to blood vessels, blood stasis, or increased coagulability, thrombin, which is also called "blood clot", forms at the topical site where the cause occurs.

Platelets, one type of blood cells, are involved in thrombogenesis, are cellular fragments having a diameter of 2 to 3 μm that include cytoplasm separated from large cells in the bone marrow, and play a key role in blood clotting.

Blood coagulation as described above is essential for survival in that it is a normal process for suppressing bleeding. However, although thrombogenesis may occur due to causes other than bleeding or is a normal process caused by bleeding, if it becomes excessive or severe, it narrows or blocks the blood vessels at the site where excessive thrombogenesis occurs, thus blocking or stopping the flow of blood. Such abnormal thrombogenesis acts as a factor that interferes with blood flow, that is, blood circulation, and may cause various cerebro-cardiovascular diseases such as blood circulation disorders, arteriosclerosis, thrombosis, high blood pressure, myocardial infarction, angina pectoris, and stroke.

Blood coagulation by platelets is induced by agonists. Examples of platelet agonists include CRPs, collagen, thrombin, thromboxane A2 analogue (U46619), and the like. CRP and collagen play an essential role in platelet aggregation in the GPVI-mediated platelet aggregation signaling pathway. In addition, thrombin, which is a thromboxane A2 analogue, plays an important role in platelet aggregation mediated by the GPCR signaling pathway.

In the experiment of the present invention, antagonism (inhibitory activity) of 2'-fucosyllactose and 3-fucosyllactose as HMOs and FOS as a positive control group was determined for four types of agonists. However, interestingly, it was found that only 2'-fucosyllactose exhibited antagonistic activity against CRP and collagen, among the four types of agonists. 3-fucosyllactose, having a structure very similar to 2'-fucosyllactose, did not exhibit antagonistic activity. In addition, 2'-fucosyllactose was found to have antagonistic activity only against CRP and collagen, among agonists, and to have no antagonistic activity against thrombin.

The absence of antagonistic activity against thrombin is of great clinical significance, because thrombin is administered in emergencies for hemostasis when bleeding occurs due to an accident or the like. When 2'-fucosyllactose of the present invention has inhibitory activity against thrombin, in addition to CRP and collagen, hemostasis becomes impossible even upon administration of thrombin in the event of an accident. In this case, it may be very dangerous to continuously consume 2'-fucosyllactose in daily life. However, surprisingly, 2'-fucosyllactose of the present invention does not inhibit the action of thrombin and thus has no problem affecting induction of hemostasis by thrombin administration in the event of an accident, even if it is consumed regularly.

In addition, when an experiment associated with carotid artery thrombosis inhibition and hemostasis was performed on an animal model, 2'-fucosyllactose of the present invention exhibited a concentration-dependent inhibitory effect against carotid artery thrombosis, which was comparable to aspirin, which is a conventional thrombosis drug. In addition, it was found that 2'-fucosyllactose did not affect the hemostasis-associated side effect of conventional synthetic drugs, which indicates that 2'-fucosyllactose is able to overcome the side effect of aspirin, which is a conventional thrombosis drug. Therefore, it was also found that 2'-fucosyllactose can be used in vivo as a health functional food or therapeutic substance for improving blood circulation.

Meanwhile, the food composition of the present invention is not particularly limited in relation to the formulation thereof, and may, for example, be selected from meats, grains, caffeinated beverages, general drinks, chocolate, breads, snacks, confectioneries, pizza, jelly, noodles, gums, ice creams, alcoholic beverages, liquors, vitamin complexes, and other health supplements such as pills, tablets, and granules.

2'-fucosyllactose may be added in an amount of 0.01 to 99% by weight to food, and the concentration of 2'-fucosyllactose in the health supplement composition is, for example, 100 to 1,000 mg, based on a 1,600 mg tablet. 2'-fucosyllactose is preferably consumed once a day for a long period of time.

Meanwhile, the pharmaceutical composition of the present invention may further contain a pharmaceutically acceptable carrier, diluent, or excipient, in addition to 2'-fucosyllactose. The pharmaceutically acceptable carrier, excipient, or diluent includes lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, and mineral oil. These may be used singly or in combination. In addition, the pharmaceutical composition may further contain a filler, anti-agglomerant, lubricant, wetting agent, fragrance, emulsifier or preservative.

Meanwhile, the formation of the pharmaceutical composition of the present invention may be prepared in a desired form depending on the method of use, and may be particularly prepared using a method known in the art selected to provide rapid, sustained, or delayed release of the active ingredient after administration to a mammal. For example, the formulation may be selected from plasters, granules, lotions, liniments, lemonades, aromatic waters, powders, syrups, ophthalmic ointments, liquids and solutions, aerosols, extracts, elixirs, ointments, fluidextracts, emulsions, suspensions, decoctions, infusions, ophthalmic solutions, tablets, suppositories, injections, spirits, cataplasmas, capsules, creams, troches, tinctures, pastes, pills, and soft or hard gelatin capsules.

Meanwhile, the dosage of the pharmaceutical composition of the present invention is preferably determined in consideration of the administration method, the age, gender, and weight of the patient, and the severity of the disease. For example, the pharmaceutical composition of the present invention is preferably administered once per day in an amount of 24 to 40 mg/kg (body weight) based on the weight of 2'-fucosyllactose. However, the dosage is merely provided as an example for illustration and may be changed as prescribed by a doctor depending on the state of the user.

Hereinafter, the present invention will be described in more detail with reference to the following examples and experimental examples. The scope of the present invention is not limited to the examples and experimental examples, and encompasses modifications of the technical concept equivalent thereto.

Example 1: Confirmation of Selective Platelet Aggregation Inhibitory Effect of HMOs (1) Experimental Purpose Whether or not HMOs have the candidate potential as a strategic substance for improving blood circulation was determined. For this purpose, in this experiment, the efficacy of 2'-fucosyllactose and 3-fucosyllactose as HMOs and FOS as a positive control on the inhibition of platelet activity and the improvement of blood circulation disorders caused by platelet action was determined.

(2) Experimental Materials and Methods

① Material

Human thrombin, thromboxane A2 analogue (U46619), PGE1, and all reagents were obtained from Sigma (St. Louis, MO). D-Phe-Pro-Arg-chloromethyl ketone (PPACK) was obtained from EMD Millipore (Billerica, Mass.). Equine tendon collagen (type I) from Chrono-log (Havertown, PA), and collagen-related peptide (CRP) provided by Dr. Richard Farndale (Department of Biochemistry, University of Cambridge, UK) were used in this experiment. Phycoerythrin (PE)-conjugated isotype control IgGs, PE anti-mouse CD62P (P-selectin) antibody, and PE anti-mouse $\alpha IIb\beta 3$ (JON/A) antibodies were obtained from BioLegend (San Diego, CA). 2'-fucosyllactose and 3-fucosyl lactose were obtained from AP Technology.

② Platelet Separation Method

Platelets were collected from the abdominal vein of mice (6-8 weeks of age) using a syringe pretreated with a citrate-dextrose solution (ACD, Sigma). After centrifugation at 300×g at room temperature for 20 minutes to obtain platelet-rich plasma (PRP), 0.5 µM PGE1 was added to the plasma isolated from red blood cells, followed by re-centrifugation at 700×g for 4 minutes. The precipitated platelets were washed with HEPES-Tyrode buffer (5 mM HEPES/NaOH, pH 7.3, 5 mM glucose, 136 mM NaCl, 12 mM $NaHCO_3$, 2.7 mM KCl) containing 10% ACD, followed by centrifugation at 700×g for 5 min. The precipitated platelets were adjusted to a concentration of $3\times10^8$ cells/mL in HEPES-Tyrode buffer and used in this experiment.

③ Platelet Aggregation Analysis Method

Mouse platelets immersed in HEPES-Tyrode buffer at a concentration of $3\times10^8$ cells/mL were pre-treated with a vehicle (distilled water), 1,000 µM FOS, 3'-fucosyllactose, and various concentrations (300 to 1,000 µM) of 2'-fucosyllactose at 37° C. for 15 minutes, and were then activated awith CRP, collagen, thrombin, and thromboxane A2 analogues in a platelet aggregation system. Platelet aggregation was induced at a rate of 1,000 rpm at 37° C. and then measured in a platelet aggregation meter (Chrono-log Corp, Havertown, PA).

④ Flow Cytometry

The activity of each of platelet P-selectin and $\alpha IIb\beta 3$, which are known biomarkers of platelet activity, was measured using a flow cytometer (Gallios, Beckman Coulter). Mouse platelets were pretreated with a vehicle (distilled water), 1,000 µM FOS and 3-fucosyllactose, and various concentrations (300 to 1,000 µM) of 2'-fucosyllactose at 37°

C. for 15 minutes, and were then activated with 0.15 ug/ml CRP at 37° C. for 5 minutes, after which the activity thereof was measured using P-selectin and αIIbβ3 antibodies.

⑤ Statistical Processing

Statistical analysis was performed based on data analysis using GraphPad Prism 5. Statistical significance was analyzed using ANOVA of multiple groups, Dunnett's test for comparisons of multiple groups, and Student's t-test for comparisons of two groups. $P<0.05$ was considered a significant result.

(3) Experimental Results

① Confirmation of Platelet Aggregation Inhibitory Efficacy of HMOs

In order to investigate the effects of HMOs on platelet function, the efficacy on platelet aggregation was first investigated.

The results are shown in FIGS. 2A to 2D. In the graph of FIGS. 2A to 2D, "light transmission" on the vertical axis is a parameter indicating that platelet aggregation increases due to increased light transmission. This is based on the principle that platelets originally floating as floating cells change in shape and aggregate when activated by platelet agonists, thus increasing light transmittance. In the graph of FIGS. 2A to 2D, "time (sec)" on the horizontal axis means a period of time of 300 seconds (sec) which is generally required for complete aggregation of platelets.

The results of this experiment show that aggregation induced by CRP (0.15 μg/ml, FIG. 2A) and collagen (0.5 μg/ml, FIG. 2B) as platelet agonists was significantly inhibited in the platelets pretreated with 2'-fucosyllactose among HMOs, in a concentration-dependent manner, compared to platelets pretreated with distilled water as the control group (vehicle). The results also show that aggregation induced by CPP and collagen was not significantly inhibited in the platelets pretreated with FOS and 3-fucosyllactose. In addition, there was no significant difference between platelets pretreated with 2'-FL and the control group in terms of the effect of inhibiting platelet aggregation induced by thrombin (0.025 U/ml, FIG. 2C) and the thromboxane A2 analogue (3 μM, FIG. 2D). That is, it was found that 2'-fucosyllactose did not exhibit an inhibitory effect on platelet aggregation induced by thrombin and thromboxane A2 analogue.

These results suggest that only 2'-fucosyllactose among HMOs plays an important role in selective platelet aggregation in the GPVI-medicated platelet aggregation signaling pathway. On the other hand, it can be seen that 2'-fucosyllactose has no inhibitory effect on the thrombin and thrombozane A2 analogue that activate platelet aggregation through the GPCR signaling pathway.

② Confirmation of Mechanism of Inhibition of Platelet Activation by HMOs

The mechanism of inhibition of platelet activation by HMOs was determined. Flow cytometry was used to analyze the efficacy of HMOs on the mechanism of regulating P-selectin and αIIbβ3 integrin activation of platelet α-granule, which is used as a platelet activation biomarker in main processes that induce a positive feedback cycle in platelet activation.

Previous platelet aggregation inhibition experiments showed that among HMOs, only 2'-fucosyllactose selectively plays an important role in platelet aggregation in the GPVI-mediated platelet aggregation signaling pathway. As a platelet activation experiment, an activation efficacy inhibition experiment was performed using only CRP.

Platelets were pretreated with a vehicle (distilled water), FOS, 2'-fucosyllactose, or 3-fucosyllactose at 37° C. for 15 minutes, and were activated at 37° C. with 0.15 μg/ml CRP for 5 minutes, after which platelet activity was measured using P-selectin and αIIbβ3 antibodies.

Figure 3A:
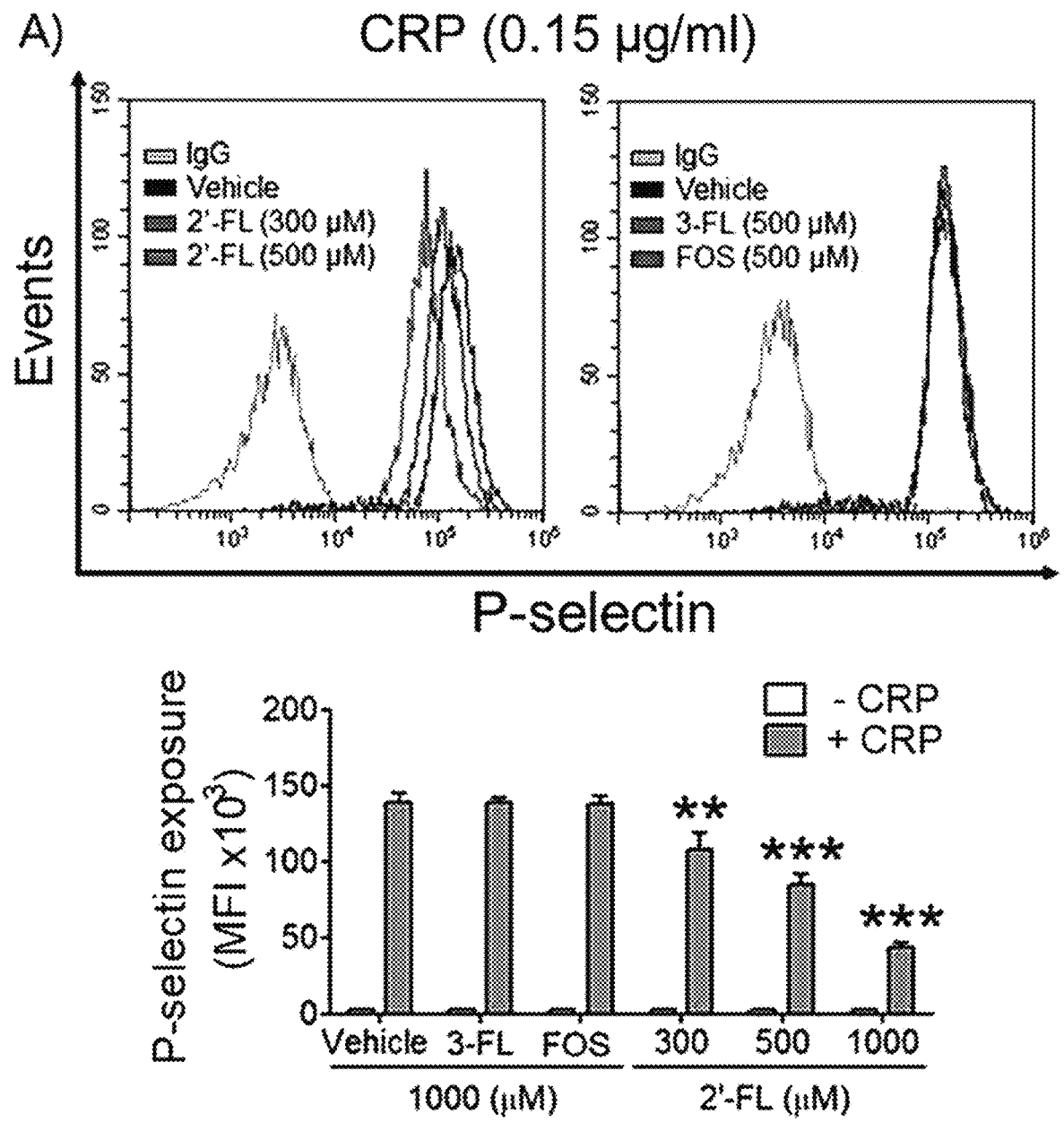
FIGS. 3A and 3B illustrate the mechanism of inhibition of platelet activation of HMOs.
Figure 3B:
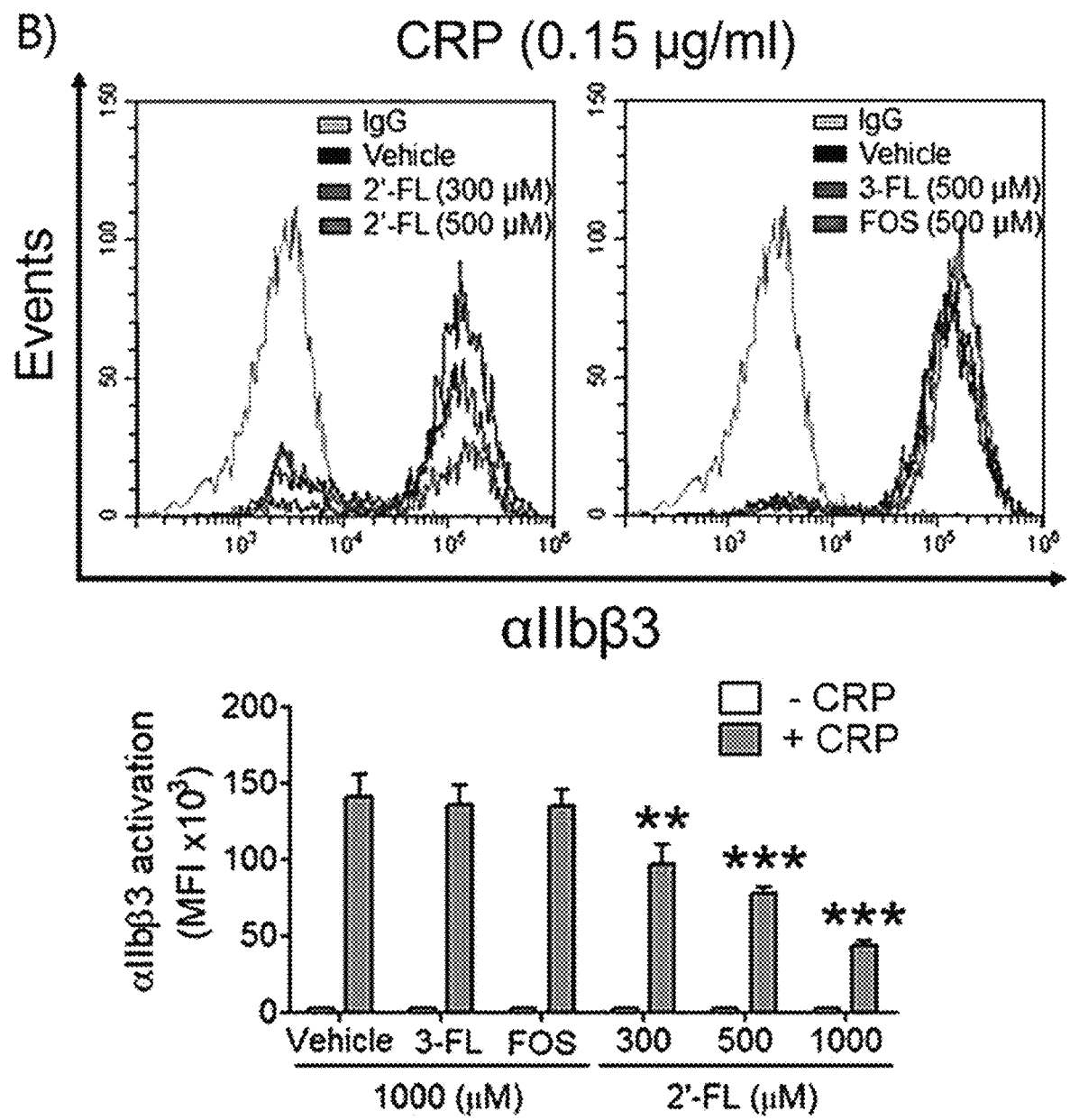

The result is shown in FIGS. 3A and 3B. When platelet activation occurs, P-selectin in α-granules was discharged from the platelet cells by a platelet activation signal, thus improving platelet activity. Increased activity of αIIbβ3, which is important for platelet-platelet aggregation, increases binding of αIIbβ3 and fibrinogen, and thus further facilitates platelet-platelet aggregation. Therefore, as parameters of platelet activities, P-selectin exposure level and αIIbβ3 activation level were measured using flow cytometry. As the peak moves to the left in the graph, the P-selectin exposure level and αIIbβ3 activation level according to platelet activity decrease. This also means that 2'-fucosyllactose has an effect of inhibiting platelet activity in a concentration-dependent manner.

The platelets pretreated only with 2'-fucosyllactose among HMOs were found to significantly inhibit activation of P-selectin of mouse platelet α-granule (FIG. 3A) and platelet αIIbβ3 integrin (FIG. 3B) in a concentration-dependent manner, compared to the control group (vehicle). These results support that 2'-fucosyllactose selectively inhibits platelet activation through granulation and inhibition of αIIbβ3 integrin activation.

Experimental Example 1: HMO Cytotoxicity Test

In this experimental example, the cytotoxicity of HMOs was evaluated by CCK assay (Oh, Y. C.; Jeong, Y. H.; Pak, M. E.; Go, Y., Banhasasim-Tang Attenuates Lipopolysaccharide-Induced Cognitive Impairment by Suppressing Neuroinflammation in Mice. Nutrients 2020, 12, (7)). No protocol for measuring cytotoxicity to platelets has been established, so HepG2 cells were pretreated with an HMO (2'-fucosyllactose or 3-fucosyllactose) in a concentration-dependent manner. After 24 hours, each well was treated with a cell-counting kit solution (Dojindo Molecular Technologies, Inc.), and further incubated for 1 hour, and then absorbance was measured at a wavelength of 450 nm using a microplate reader.

Figure 4:
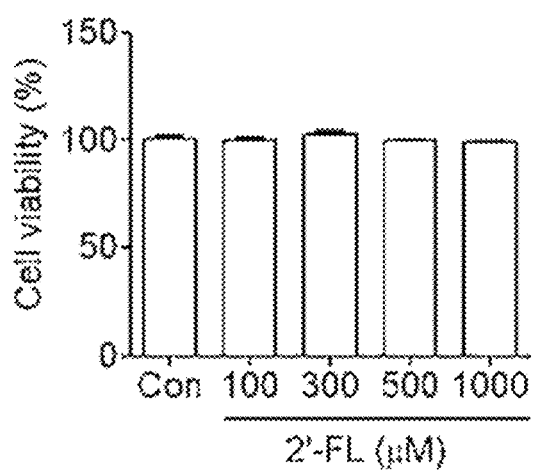
FIG. 4 shows the cytotoxicity of HMOs, measured through a CCK assay.
Figure 4:
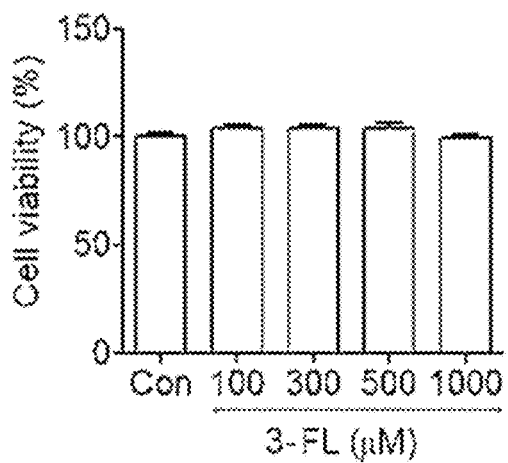

The HepG2 cells was pretreated with HMO, and the cell viability thereof was measured. As a result, as can be seen from FIG. 4, cell death of HepG2 caused by the treatment with HMOs (2'-fucosyllactose, 3-fucosyllactose) was not observed, which indicates that the HMO was non-cytotoxic.

Example 2: Confirmation of Blood Circulation Improvement-Associated Platelet Activity (In Vivo) of HMOs (1) Experimental Purpose In this experiment, the blood circulation improvement efficacy of HMOs in an animal model of carotid artery ligation thrombus was evaluated, and the platelet aggregation and activation efficacy after oral administration (ex vivo) thereof were determined.

(2) Test Animal Preparation and Test Method

① Preparation of test animals

Male C57BL/6 mice (6-8 weeks old) used in the experiment were purchased from Dooyeol Biotech Co., Ltd., were acclimatized for a predetermined period at 23±1° C. and 56% relative humidity while a general diet was provided thereto for 1 week, and were then used for the experiment. In the following, animal experiments were performed in accordance with the guide for the animal study protocols approved by the Korea Institute of Oriental Medicine Institutional Animal Care and Use Committee (approval number: 20-058).

② Production of thrombosis animal model using $FeCl_3$ and Measurement of Blood Flow $FeCl_3$ (10%) was used to establish a thrombosis-induced mouse model. Mice were orally administered with 2'-fucosyllactose (500, 1,000 mg/kg BW), 3-fucosyllactose (1,000 mg/kg BW), or ASA (100 mg/kg BW) for 7 days. 2 hours after the last administration, the mice were anesthetized with 2% isoflurane, the left carotid artery was isolated from each mouse, and filter paper (2 mm in diameter) soaked with $FeCl_3$ (10%) was placed on the carotid artery for 2 minutes to induce thrombosis. Blood flow was measured using a blood flow meter (AD meter).

③ Production of Tail Bleeding Time Animal Model and Measurement of Hemostasis

A tail bleeding time assay was performed to measure hemostasis caused by thrombosis. The mice were orally administered with 2'-fucosyllactose (500 or 1,000 mg/kg of BW), 3-fucosyllactose (1,000 mg/kg of BW), or ASA (100 mg/kg of BW) once a day for 7 days. 2 hours after the last administration, the mice were anesthetized with 2% isoflurane. Then, the tail of each mouse was cut to a size of 5 mm using a razor blade and immobilized in a 50 mL conical tube containing 45 mL of PBS, after which the bleeding time and amount of blood were measured. The specific process and image are shown in A of FIG. 6. The blood flow loss was quantified by measuring the content of blood hemoglobin collected with 45 mL of PBS. At this time, the body temperature was maintained at 37° C. using a heating pad.

④ Statistical Processing

Statistical analysis was performed based on data analysis using GraphPad Prism 5. Statistical significance was analyzed by ANOVA of multiple groups, Dunnett's test for comparisons of multiple group, and Student's t-test for comparisons of two groups. $P<0.05$ was considered a significant result.

(3) Experimental Results

① Confirmation of Efficacy of Inhibition of Thrombosis Formation of HMOs in Carotid Artery Thrombosis Animal Model When blood vessels are damaged, platelets are activated and aggregate at the damage site to stop bleeding attributable to the damage to the blood vessels, but cause thrombus under pathological/pathophysiological conditions, and platelet activity plays an essential role at this time.

Figure 5:
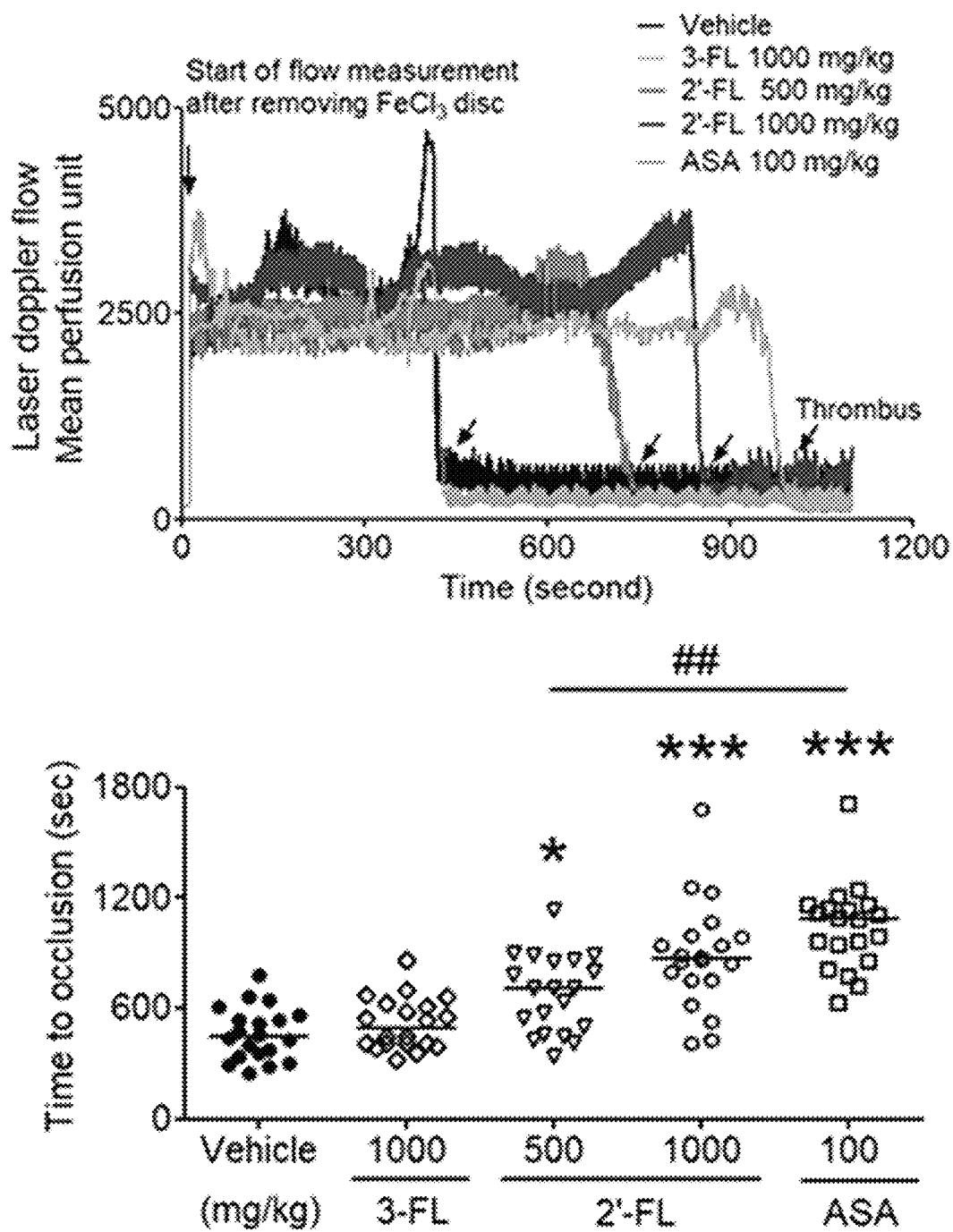
FIG. 5 shows the thrombosis inhibitory efficacy of HMOs in an animal model.

The efficacy of inhibition of thrombosis in the thrombosis-induced mouse model was determined. As can be seen from FIG. 5, the result showed that the control group (vehicle) exhibited an average carotid artery occlusion time of 7.47 minutes, the group administered with a low concentration (500 mg/kg BW) of 2'-fucosyllactose exhibited an average carotid artery occlusion time of 11.79 minutes, and the group administered with a high concentration (1,000 mg/kg BW) of 2'-fucosyllactose exhibited an average carotid artery occlusion time of 14.52 minutes. That is, the average carotid artery occlusion time significantly increased in a 2'-fucosyllactose-concentration dependent manner. In contrast, the group administered with a high concentration (1,000 mg/kg BW) of 3-fucosyllactose exhibited a carotid artery occlusion time of 8.18 minutes, which was not significantly different from that of the control group. In addition, the group administered with a high concentration (1,000 mg/kg BW) of 2'-fucosyllactose exhibited a prolonged carotid artery occlusion time, comparable to 18.05 minutes for the group treated with aspirin (100 mg/kg BW) as a positive control group (represented by ASA).

② Confirmation of Hemostatic Effect of HMOs in Carotid Artery Thrombosis Animal Model When blood vessels are damaged, platelets are activated and thus aggregate and adhere to the damage site, thereby acting as a hemostatic agent to suppress bleeding due to the damage to blood vessels. In this experiment, how 2'-fucosyllactose, which exhibited concentration-dependent inhibitory activity in carotid artery thrombosis, affected hemostasis was determined.

Figure 6:
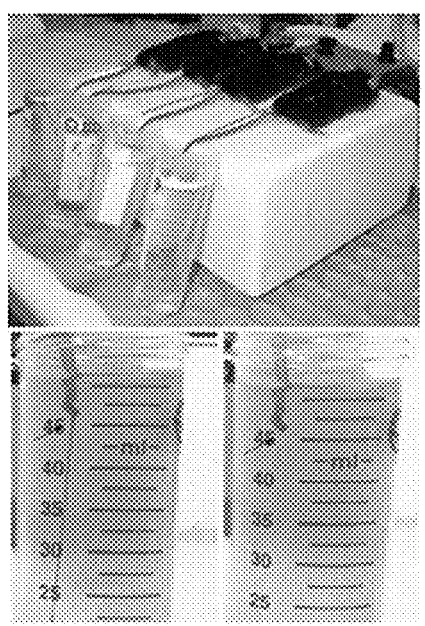
FIG. 6 shows the hemostatic efficacy of HMOs in an animal model.
Figure 6:
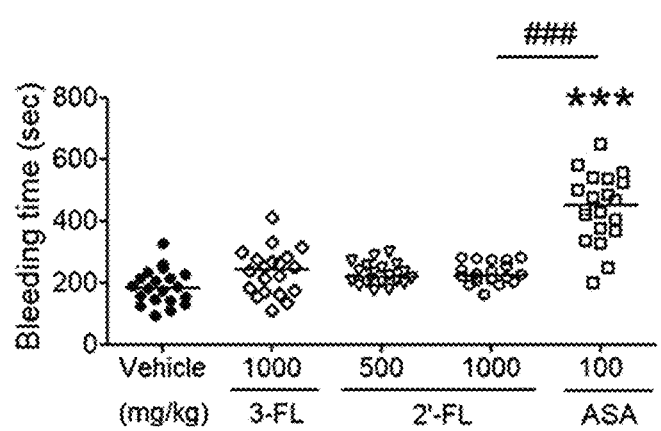
Figure 6:
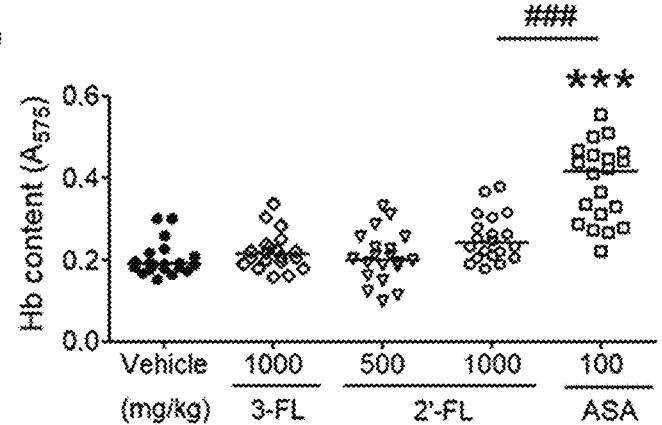

The bleeding time and blood amount of the tail cut from the thrombosis-induced mouse model were measured. The result, as shown in B of FIG. 6, showed that there was no statistically significant difference between the group administered with a high concentration of 3-fucosyllactose and the group administered with a high or low concentration of 2'-fucosyllactose and the control group. In addition, the content of each of blood and hemoglobin collected from the cut site was quantified compared to the control group. As shown in C of FIG. 6, the result showed that the amount of blood loss in the mice fed with a HMO was not significantly different from that of the control group. However, when 100 mg/kg BW of ASA was orally administered to the mice for 7 days, the bleeding time and hemoglobin content were greatly increased compared to the group administered with 2'-fucosyllactose and the control group. These results showed that the HMO is useful as a therapeutic substance that can overcome the side effects of aspirin, which is a conventional antithrombotic drug.

As is apparent from the foregoing, the 2'-fucosyllactose of the present invention exhibits antagonistic (inhibitory) activity against CRP and collagen, which are agonists of platelets, and can be used to inhibit thrombogenesis due to abnormal platelet activity. Therefore, continuous consumption or administration of the 2'-fucosyllactose of the present invention enables amelioration of various cerebro-cardiovascular diseases caused by thrombogenesis, such as blood circulation disorders, arteriosclerosis, thrombosis, hypertension, myocardial infarction, angina pectoris, and stroke.

Meanwhile, it was found that 2'-fucosyllactose exhibited antagonistic activity only against CRP and collagen, which are agonists of platelets, but did not exhibit antagonistic activity against thrombin used for hemostasis in emergency situations. The absence of antagonistic activity against thrombin is of great clinical significance, because thrombin is administered in emergencies for hemostasis when bleeding occurs due to an accident or the like. If 2'-fucosyllactose of the present invention has inhibitory activity against thrombin, in addition to CRP and collagen, hemostasis is impossible even by administration of thrombin in the event of an accident. If so, it may be very dangerous to continuously consume 2'-fucosyllactose in daily life. However, surprisingly, 2'-fucosyllactose of the present invention does not inhibit the action of thrombin and thus causes no problem related to induction of hemostasis by thrombin administration in the event of an accident, even if consumed regularly.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for ameliorating a cerebro-cardiovascular disease caused by a thrombus, comprising administering a composition comprising 2'-fucosyllactose (2'-FL) to a subject in need thereof.

2. The method according to claim 1, wherein the thrombus is formed due to blood clotting by platelets.

3. The method according to claim 2, wherein the blood clotting by platelets is caused by an action of collagen-related peptide (CRP) or collagen, which is an agonist of platelets.

4. The method according to claim 1, wherein the cerebro-cardiovascular disease is any one selected from blood circulation disorders, arteriosclerosis, thrombosis, hypertension, myocardial infarction, angina pectoris, and stroke.

* * * * *